United States Patent [19]

Kude et al.

[11] 4,359,284
[45] Nov. 16, 1982

[54] METHOD AND APPARATUS FOR DETERMINING THE WOBBE INDEX OF GASEOUS FUELS

[75] Inventors: William B. Kude, Plymouth; A. Noel J. Pearman, St. Paul, both of Minn.

[73] Assignee: Honeywell Inc., Minneapolis, Minn.

[21] Appl. No.: 244,539

[22] Filed: Mar. 17, 1981

[51] Int. Cl.³ ............................................ G01N 25/22
[52] U.S. Cl. ..................................................... 374/37
[58] Field of Search .............. 73/190 CV; 422/51, 54, 422/98

[56] References Cited

U.S. PATENT DOCUMENTS

| | | | |
|---|---|---|---|
| 3,393,562 | 7/1968 | Breedlove | 73/190 |
| 3,783,684 | 1/1974 | De Livois | 73/190 |
| 4,315,430 | 2/1982 | Szonntagh | 73/190 |

FOREIGN PATENT DOCUMENTS

| | | | |
|---|---|---|---|
| 961666 | 1/1975 | Canada | 73/97 |
| 8151 | 2/1980 | European Pat. Off. | |

*Primary Examiner*—Herbert Goldstein
*Attorney, Agent, or Firm*—Charles G. Mersereau

[57] ABSTRACT

A method and apparatus for determining the Wobbe Index of gaseous fuels is disclosed in which a mixture of sample fuel, the flow of which is monitored by pressure differential across a flowmeter, and a substantially constant amount of air is burned in the presence of an electrochemical sensor which exhibits a rapid change in output signal about a certain combustion product composition. The fuel content of the mixture is adjusted in response to the sensor output signal until the certain combustion product composition is attained and the Wobbe Index determined from a known relationship between the heating value of the fuel constituents and the amount of oxygen required for the combustion thereof at said certain combustion product composition and the pressure differential across the fuel flowmeter. Calibration of the system may be accomplished with standard gases.

14 Claims, 7 Drawing Figures

TYPICAL ELECTROCHEMICAL SENSOR RESPONSE

*Fig. 7*

METHOD AND APPARATUS FOR DETERMINING THE WOBBE INDEX OF GASEOUS FUELS

BACKGROUND OF THE INVENTION

1. Field of the Invention

The present invention relates generally to the field of measuring and monitoring the heating value of gaseous fuels such as natural gas and, more particularly, to a method and apparatus for determining and monitoring the Wobbe Index of such fuels on a real-time basis.

2. Description of the Prior Art

The heating values of gaseous fuels such as those largely containing alkane hydrocarbons are frequently given assumed average numbers; thus the heating value of natural gas, for example, is frequently assumed to be 1000 British Thermal Units (BTU's) per cubic foot. In the past, pricing of such fuels has been based upon either the assumption of a nominal average value or by the periodic checking of the actual value by a variety of time-consuming methods.

In one method chromatographic analysis of the constituents has been used to compute the actual heating value or BTU content of a given natural gas from the percentage composition of the mixture. In another method the heat content has been determined by measuring the amount of heat liberated in burning exactly one cubic foot of gas (saturated with water) at standard conditions of temperature and pressure. The heat so liberated is absorbed by a weighted amount of water and the subsequent temperature rise of the water used to calculate the gross or "higher heating value".

These methods involve reasonably expensive instrumentation and require considerable labor to perform the measurements and calculations. Such testing, of necessity, introduces considerable time delay and certainly appears less desirable than an on-line, real-time system. Even so, these might be sufficient methods if, in fact, the composition of the gas being used did not vary greatly with time. However natural gas, for example, may vary greatly in composition depending on the gas fields from which it came and the treatment it receives before distribution. The gas that reaches the customer consumers frequently is only about 85% methane with the remaining 15% being a mixture of various hydrocarbon molecules such as ethane, propane, n-butane, i-butane, etc. Also, as much as 25% of the gas reaching the customer may be made up of non-combustible constituents which occur naturally or have been added to the mixture. These include nitrogen, air and carbon dioxide. Natural gas is used herein as a representative example because it is by far the most widely used gaseous fuel.

The inerts, of course, add nothing to the heating value, and the heating value of alkane, and other hydrocarbons of higher order than methane have a higher heating value on a volumetric basis because of their higher molecular weight. In view of the great variation in constituents of natural gas, the heating value even in a single distribution system may vary greatly with time.

As a result of these and other factors, a random sampling of the heat content of the natural gas being distributed, might lead to great inaccuracies as to the actual heating value of the fuel delivered. As the price of natural gas has increased greatly, it has become necessary for the heat content of the natural gas to be continually monitored and adjusted in order to stay within promised specified limits and to insure that the user is charged for the proper amount of heating value he receives from the fuel.

One such on-line device for the continual monitoring of the higher heating value of such fuels is illustrated and described in present pending application Ser. No. 105,794 filed Dec. 20, 1979, and now abandoned, by William B. Kude and A. Noel J. Pearman, co-inventors in the present application, and Daniel L. Youngbauer. That application is assigned to the same assignee as the present invention.

By that invention there is provided an on-line fuel BTU meter which includes a precise, adjustable metering system which accurately proportions an amount of fuel gas or calibration gas to be tested with a known amount of air such that, at any given time, the volumetric ratio of air to fuel is precisely known. The mixture is fed to a burner system in which the fuel is combusted in the presence of a solid-state ceramic electrochemical cell which provides a step-change in voltage output as the amount of residual oxygen or combustibles, a certain repeatable amount, which, in the preferred embodiment approaches zero, that is, approaches the point of stoichiometry. An electrical signal from the electrochemical cell is utilized with a programmable electronic data processing system to adjust the fuel mixture in accordance with the signal output of the electrochemical cell to achieve and maintain the stoichiometric air-fuel ratio as signalled by the rapid change in electrical output of the cell at that point. The air-fuel ratio at that point is known from the measuring system and the heat content is known from the measuring system and the heat content of the fuel is readily determined based on the known constant relationship between the stoichiometric air-fuel ratio and the fuel heat content.

Whereas the BTU meter of the above-mentioned patent application presents a highly accurate on-line system for monitoring the heat content of gaseous hydrocarbon fuels on a volumetric basis, another very important dimension should be added to account for changes in the specific gravity of the fuel so that a constant heat input to a pressure fueled burner system can be maintained. Thus, the utility companies are very much concerned that the customer be charged precisely for the amount of heat value sold on a volumetric basis, those utilizing the gaseous fuel are also concerned that the specific gravity be considered so the burner energy input remains constant, whatever the relative BTU content be on a volumetric basis. Variations in burner efficiency can be very costly especially in industrial burner applications.

Accordingly, changes in the density or specific gravity of the fuel should be considered in addition to the heating value of the fuel on a volumetric flow basis in order to assure constant heat input to the burners. Such may be accomplished by determining and monitoring the Wobbe Index of the fuel which is defined as follows:

$$W_o = H_v(sg)^{-0.5}$$

where:

$H_v$ is the higher heating value of the fuel in BTU's/ft$^3$ and sg = the specific gravity of the fuel.

It is apparent from the above that by considering changes in the specific gravity of the fuel gas in addition to the heating value on a standard volumetric basis, the Wobbe Index is useful as a measure of the potential heat production available for a given burner input. Thus, a fuel mixture of constant Wobbe Index will provide constant heat input to a burner system. Because of the great variation in the heating value of gaseous fuels the Wobbe Index has long been used in connection with providing a more constant heating value input to burner systems to produce better system stability. In the past, however, in order to determine the Wobbe Index of a fuel gas, separate calorimetry and density measurements had to be made and the results combined. This involved the use of expensive calorimeters and density meters and required considerable time to obtain usable results. It was not possible to obtain the desired real-time Wobbe Index Control in an industrial setting.

In the prior art, attempts have been made to measure perameters related to the Wobbe Index and use these to, in turn, monitor or control burner input. One such prior art scheme is found in a patent to Krijgsman, European Patent No. 0 008 151, issued Feb. 20, 1980. That invention basically uses the oxygen measurement of the products of combustion of a completely combusted sample at constant volumetric air and gas flow to correlate to the Wobbe Index. A fuel sample is withdrawn from a sample stream containing a flow nozzle in a manner in which the pressure drop across the flow nozzle and thus the flow is kept constant. The sample is burned in a combustion chamber combined with a control stream of combustion air. The oxygen content of the products of combustion is measured and the Wobbe Index is derived from the measured oxygen content. Thus, the device operates at known constant sample flow and known constant oxygen supply to the burner and the Wobbe Index is mathematically correlated with the oxygen measurement in the exhaust gas. The preferred mode of operation is with an excess amount of oxygen in the exhaust gas, for example, at 5% oxygen. The Wobbe Index is thus derived directly from the oxygen content of the products of combustion. The measurement apparatus of that invention is utilized to control the mixing apparatus by means of which gases having different Wobbe Indices can be combined to produce a heating gas with a constant Wobbe Index.

Another prior art device is illustrated and described in a patent to De Livois, U.S. Pat. No. 3,783,684 issued Jan. 8, 1974. That invention is concerned with providing constant fuel heat content flow in a burner system. The device utilizes a calorimeter system in which the fuel input is adjusted such that the temperature rise in the calorimeter remains constant for a constant amount of supplied combustion air. In this manner the fuel supplied to an entire combustion system may also be adjusted based on the fuel necessary to keep the calorimeter temperature rise at a given desired value. This is accomplished by pressure drop control across supply orifices, thus, that invention presents a direct control system based on calorimetry rather than a system for measuring the actual Wobbe Index of the fuel.

While these and other prior art devices have been somewhat successful in providing on-line-measurement of Wobbe Index related perameters, they lack a single accurate reference point from which to base such measurements.

SUMMARY OF THE INVENTION

By means of the present invention there is provided a simplified, repeatably accurate method and apparatus for determining the Wobbe Index of gaseous fuels. In the present invention a substantially constant amount of combustion air is provided to a sample burner along with an amount of sample fuel gas which can be accurately and automatically modulated. The signal from an oxygen sensor is utilized to control the flow of sample fuel gas supplied to the burner such that the percent oxygen contained in the exhuast gas is controlled about a value where the sensor is highly accurate. Provision is also made for accurately measuring the pressure drop of the fuel flow across an orifice meter or similar device. The BTU content of the fuel can be accurately measured and the Wobbe Index instantaneously calculated from the known pressure drop accross the fuel metering orifice utilizing this system.

In one illustrative embodiment a predetermined fuel-air mixture is fed to a burner system in which the fuel is combusted in the presence of a solid-state ceramic electrochemical cell similar to that utilized in the above-mentioned co-pending application Ser. No. 105,794 which provides a step-change in voltage output as the amount of residual oxygen or combustibles approaches a certain repeatable amount which in the preferred embodiment approaches zero, that is, at or near the point of stoichiometry. The electrical signal from the electrochemical cell is used from a programmable electronic processing system to modulate the amount of sample fuel in the mixture in accordance with the output of the electrochemical cell to achieve and determine the stoichiometric air-fuel ratio as signalled by the rapid change in electrical output of the cell at that point. The relative amount of air and fuel supplied at that point is known from the measuring system and the Wobbe Index of the fuel is readily determined therefrom. The result, of course, is a simple, highly accurate Wobbe Index monitor which takes advantage of the high sensitivity of a ceramic sensor in combination with a fuel flow in the range which makes the fuel flow measurement extremely accurate.

DESCRIPTION OF THE PREFERRED EMBODIMENTS

Figure 1:
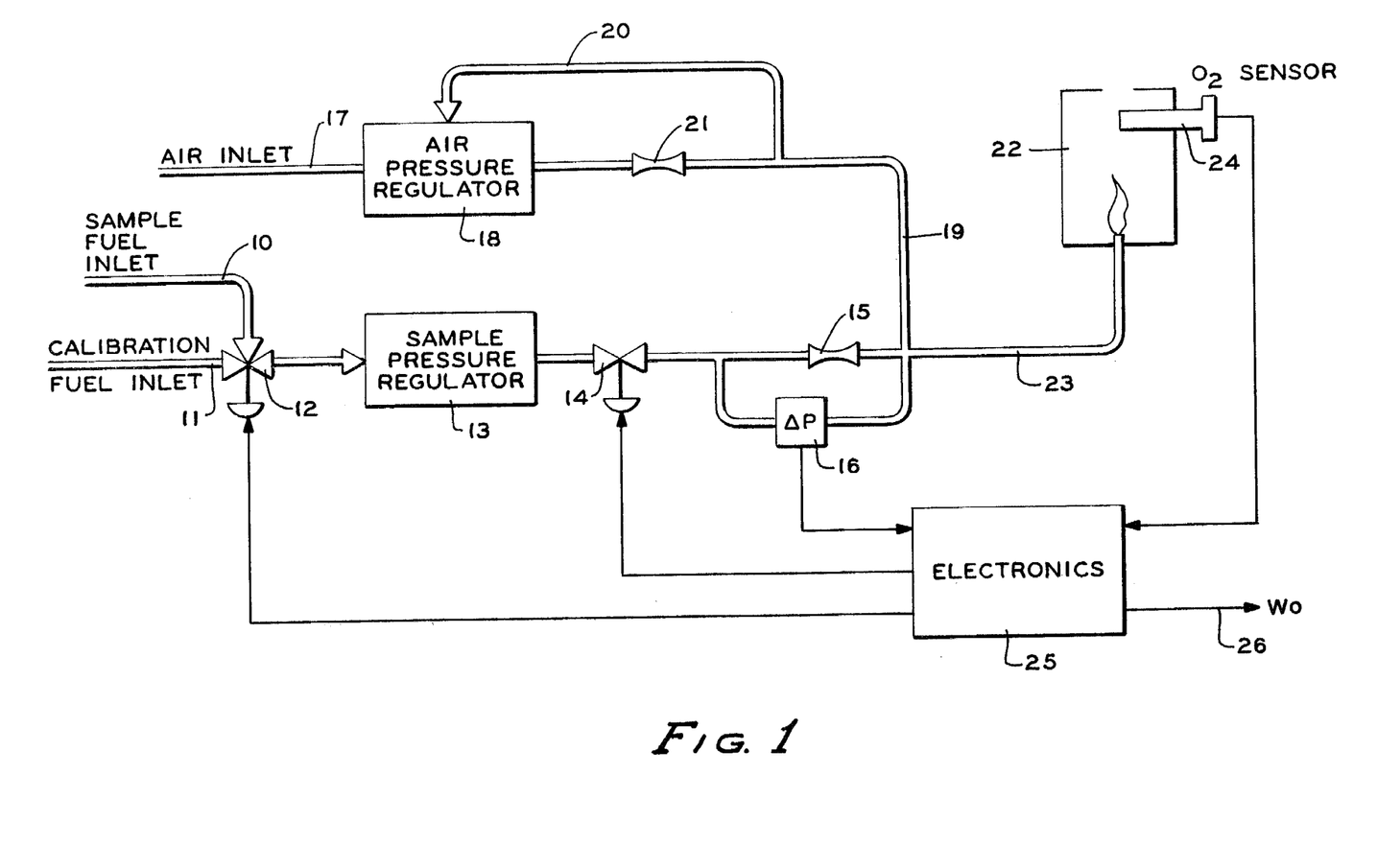
FIG. 1 is a schematic diagram of one embodiment of the Wobbe meter of the invention.

In FIG. 1 there is depicted a schematic diagram of one embodiment in accordance with the present invention. This includes a sample fuel inlet 10 which, with calibration gas inlet 11, is adapated to supply either sample fuel or calibration gas to the system from suitable sources thereof as through an electrically controlled two-position, three-way valve 12 which admits the selected components to the system through pressure regulator 13. A flow control valve 14, which may be any suitable type of flow control valve which can be accurately modulated electrically, such as a needle valve is provided to control the sample flow input to the system. A metering orifice 15 in conjunction with a sensitive orifice pressure transducer 16 is utilized to accurately measure the sample fuel input to the system.

Combustion air is supplied to the system through an air inlet 17, which may be supplied from a combustion air blower or other source of pressurized air. The pressure is regulated by pressure regulator 18 which is backloaded from the common air-gas line 19 as at 20 and a metering orifice 21. The sample burner shown at 22 is supplied with the air-gas mixture through line 23 and the products of combustion are sensed as by sensor 24. The necessary control and data processing functions are performed by electronics shown at 25 and the Wobbe Index output, which may be in the form of a digital register, recorder, direct controller or other means is indicated at 26.

Figure 2:
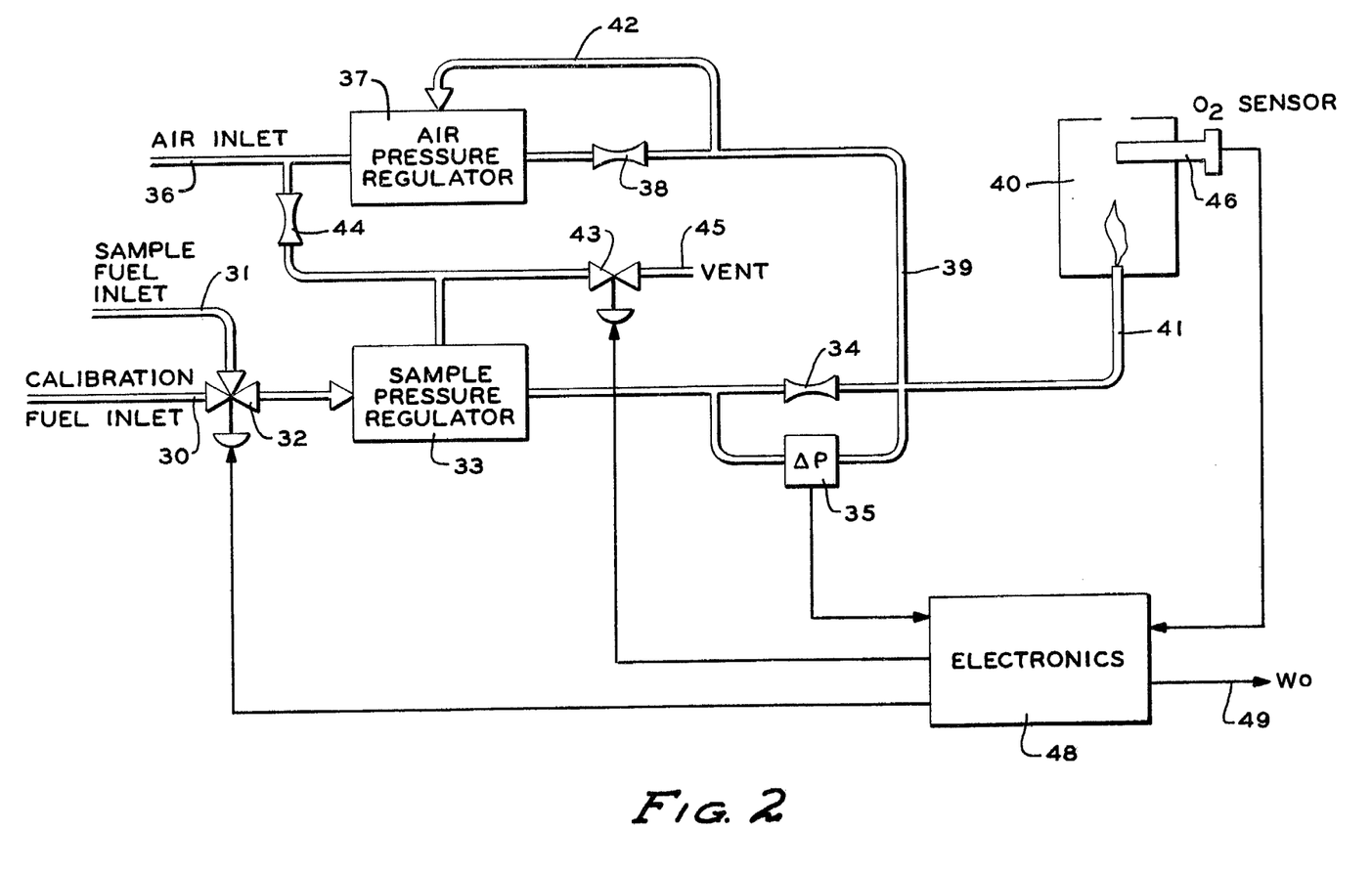
FIG. 2 is a schematic diagram of an alternate to the embodiment of FIG. 1.

FIG. 2 depicts an alternate form of the embodiment shown in FIG. 1 including, calibration gas inlet 30 which along with sample fuel inlet 31 are connected repectively to the corresponding sources of supply, two-position, three-way valve 32 and fuel sample pressure regulator 33 along with metering orifice 34 and orifice pressure transducer 35. Air from a suitable source enters at 36 and proceeds through pressure regulator 37 orifice 38 and is combined with the fuel in line 39. The mixture is supplied to the burner 40 through line 40. The air pressure regulator is backloaded from line 39 as at 42. The system also contains a flow control valve 43 which replaces the valve 14 of FIG. 1 and may be the same type of valve. One port of the valve 43 is connected to the source of combustion air through a metering orifice 44 which is also commonly connected as a backload on regulator 33 and the other port is open to vent at 45. Controlled back pressure is applied to regulator 33 modulating the amount of venting of valve 43 thereby controlling the fuel pressure and fuel flow rate. This control scheme offers the advantage of enabling the entire sample output pressure of the regulator 33 to be placed across the metering orifice 34 by eliminating the pressure drop across the needle valve 14 of FIG. 1. An oxygen sensor 46 necessary electronics 48 without output 49 are also provided.

Figure 7:
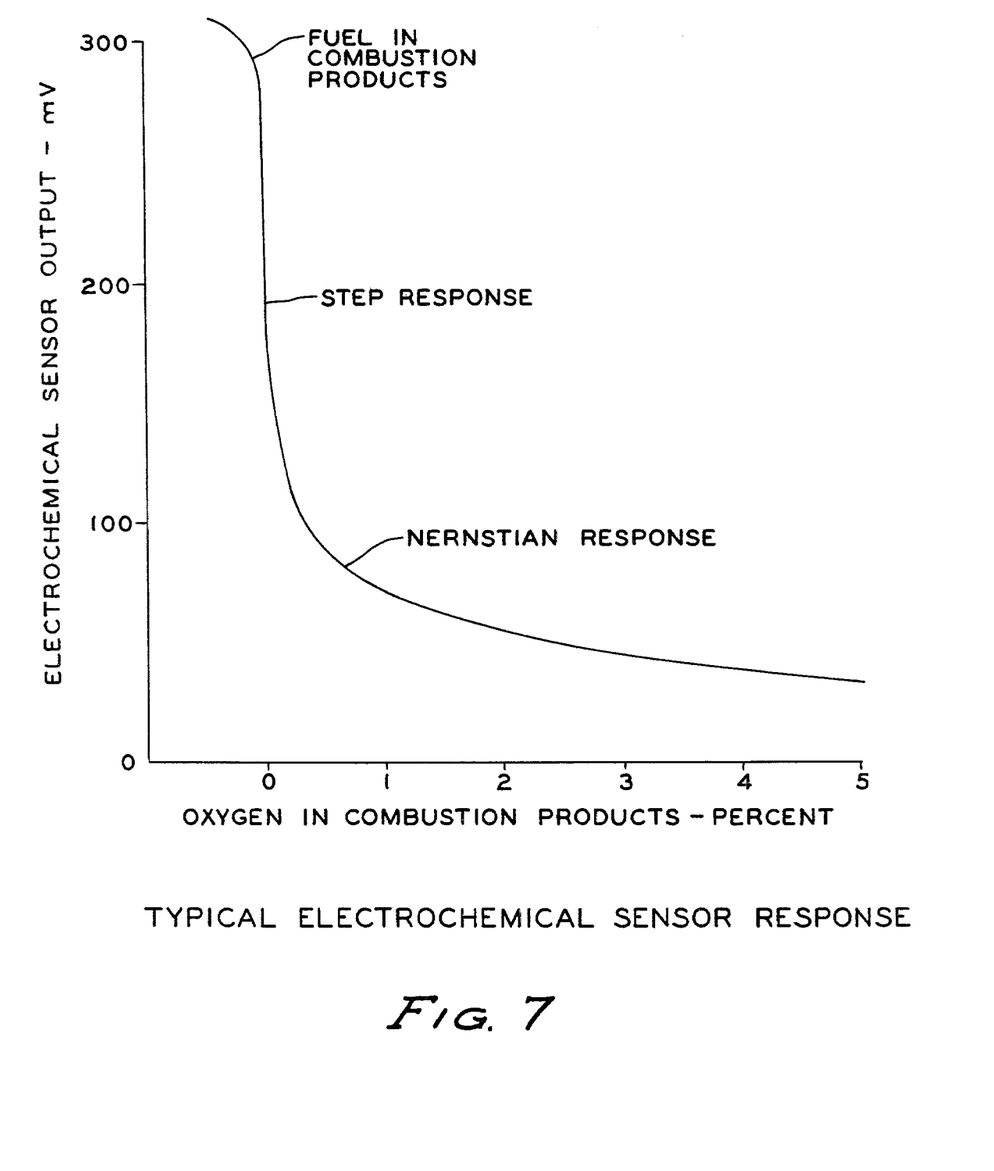

It should be noted that one of the key advantages with regard to the increased accuracy and successful operation of the Wobbe meter in accordance with the present invention lies in the ability to accurately sense the amount of oxygen in the products of combustion. Under normal conditions, natural gas or other such fuel is burned with an excess of oxygen to assure complete combustion and an absence of carbon monoxide in the products of combustion. This leads to the presence of an amount of excess oxygen after combustion which lends itself to the use of solid electrolyte-based oxygen sensors. The preferred ceramic based electrochemical sensor is made chiefly of Zirconia ($ZrO_2$) which is known to exhibit a Nernstian Voltage output response when exposed to differing partial pressures of oxygen on each side of the ceramic material. A typical response curve of such material is depicted in FIG. 7. Such a sensor can be used to sense the amount of oxygen present in the products of combustion and, as can be seen from the curve, is characterized by an extremely rapid change in voltage output at or very near the stoichiometric point. It may also be noticed that the accuracy of the sensor output, i.e. rate of change of voltage with change of oxygen content in the products of combustion is much less as one proceeds away from the substantially stoichiometric point.

It has been found that sensor output is decidedly temperature sensitive in the presence of more than minute amounts of oxygen. Thus, when operating in the oxygen rich portion of the $ZrO_2$ electrochemical response curve the temperature of the sensor must also be carefully controlled. When operating on or about the stoichiometric point, however, the output is substantially stable over a wide temperature range, i.e., from about 800° C. to 1400° C., and therefore temperature control in the combination chamber is not critical. In fact, the relative size of the combustion chamber 22 or 40 is normally sized in accord with the amount of fuel to be burned such that the temperature within the chamber is maintained within the limits where the sensor is not temperature sensitive at or about the stoichiometric point of combustion.

It should be noted that the $ZrO_2$ sensors are normally stabilized with amount of CaO, MgO or $Y_2O_3$ to further stabilize the temperature related response and to enhance the chemical and physical stability of the Zirconium Oxide for use as a sensor. This results in a stable sensor which possesses almost a step-change response at, or about the point of mixture stoichiometry. A more complete explanation of the operation and makeup of such sensors is found in the above-mentioned copending application Ser. No. 105,794 which specification is hereby incorporated by reference to the extent necessary for a more complete description.

Before describing other embodiments in accordance with the present invention, the use of the stoichiometric point in the combustion of the sample gas which contains a mixture of alkane hydrocarbon fuels will be more fully developed. The stoichiometric combustion equation for methane, the chief component of natural gas fuels, is given by the following equation which assumes that the air utilized for combustion comprises 20.83% $O_2$ and 79.17% $N_2$ and other inerts:

$$CH_4 + 2(O_2 + 3.76N_2) \rightarrow CO_2 + 2H_2O + 7.52N_2$$

Therefore, wherein $$A/F_{CH_4}$$

represents the air-fuel ratio of methane $$A/F_{CH_4} = (2)(4.76)/1 = 9.52$$

Table I represents stoichiometric air-fuel ratios of various alkane hydrocarbons through pentane and adds a column Hv which represents the higher or gross heating value of each particular specie in units of BTUs per cubic foot at 68° F., 14.7 PSIA which are derived MARKS Mechanical Engineering Handbook, Seventh Edition (McGraw-Hill N.Y. 1958). The Hv includes the latent heat of vaporization for steam formed in the combustion reaction. It should be noted that in deriving the actual air-fuel ratios, a value of 0 has been assigned to inerts which normally carry through the system unchanged and an arbitrary value of minus 4.76 has been assigned to each $O_2$ based on its combination with alkane hydrocarbons in the combustion reaction.

TABLE I

| SPECIE | A/F | Hv* |
|---|---|---|
| $CH_4$ | 9.52 | 994.7 |
| $C_2H_6$ | 16.66 | 1742.6 |
| $C_3H_8$ | 23.80 | 2480.1 |
| $C_4H_{10}$ | 30.94 | 3215.6 |
| $C_5H_{12}$ | 38.08 | 3950.2 |
| INERTS | 0 | 0 |
| $O_2$ | −4.76 | 0 |

*BTU/FT³ AT 68° F., 14.7 PSIA (MARKS)

In view of the above, for a sample of mixed saturated alkane hydrocarbons, inerts and oxygen, the air-fuel ratio of a sample ($A/F_s$) may be represented by $$A/F_s + 9.52x_1 + 16.66x_2 + 23.8x_3 + 30.94x_4 + 38.08x_5 - 4.76x_7$$

wherein the x subscript represents the fraction of that hydrocarbon constituent having the given number of carbon atoms through 5 and the 7 has been assigned to oxygen. The higher heating value of the same ($Hv_s$) then can be given by $$Hv_s = \sum_{i=1}^{5} (Hv_i)(x_i)$$

where $Hv_i$ is the higher heating value of the $i^{th}$ fuel gas constituent and $x_i$ is the fraction of the $i^{th}$ constituent in the fuel gas. As can be seen from the embodiments of FIGS. 1 and 2 the fuel flow rate can be accurately controlled in the case of FIG. 1 by the motorized needle valve or similar controllable valve 14 in conjunction with the orifice 15 and in the case of FIG. 2 with the motorized or similar bleed valve 43 in conjunction with the backloading system including orifice 44 and vent 45. The air, of course, is also suitable pressure regulated as seen in those figures. After the fuel and air are mixed and burned in the chambers 22 or 40, the sensor 24 or 46 is used in conjunction with the electronics to achieve and maintain substantially stoichiometric proportions for the combustion of the sample gas by controlling the fuel flow.

When substantially stoichiometric combustion is achieved in the chamber the differential pressure measurement measured as by pressure transducer sensors 16 and 35 may be utilized to calculate the actual Wobbe Index in the manner which will be presently discussed.

The fuel conduits and the orifices 15 or 34, as the case may be, are sized such that the differential pressure measurement ($\Delta P$) across the measuring orifice is very small. Also, the fuel gas is sufficiently above its vaporization point that the well-known orifice equation for incompressible fluids can be used as follows:

$$Q_f = C_D A \left( \frac{2(P_1 - P_2)}{\rho_f [1 - (d_2/d_1)^4]} \right)^{0.5} \quad (1)$$

where $Q_f$ is the volumetric flow rate through the orifice $C_D$ is the experimentally determined discharge coefficient, A is the area of the orifice opening $d_1$ and $d_2$ are the pipe inside diameter and orifice opening diameter, respectively $1 - (d_2/d_1)^4$ is the correction for the velocity of approach $P_1$ and $P_2$ are the upstream and downstream fuel orifice pressures, respectively, in units of force per unit area.

$\rho_f$ is the fluid density in mass per unit volume

Now $$P_1 - P_2 = \Delta P \quad (2)$$

measured across the fuel orifice and $$C_D A (2/1 - (d_2/d_1)^4)$$

is constant for a given orifice; therefore we may rewrite Equation 1 for fuel:

$$Q_f = K(\Delta P/\rho_f)^{0.5}$$

where $$K = C_D A (2/[1 - (d_2/d_1)^4])^{0.5} \quad (3)$$

Rearranging Equation 3 we have:

$$(\rho_f)^{0.5} = K(\Delta P)^{0.5}/Q_f \quad (4)$$

Let the heating value of the fuel be $Hv_s$, therefore from FIG. F we have:

$$Hv_s = 103.68(A/F_s) + 7.67 \quad (5)$$

If the fuel is basically natural gas or methane ($CH_4$) in the region of intersest, Hv = 800–1200 BTu/SCF).

Equation 5 may be approximated by:

$$Hv = K_1 Q_a / Q_f \quad (6)$$

where $$k_1 \simeq 104.$$

It will be recalled that the Wobbe Index is defined as $$Wo = Hv(sg)^{-0.5}$$

Now the Wobbe Index may be given by:

$$Wo = Hv(\rho_f/\rho_a)^{-0.5} \quad (7)$$

or $$Wo = Hv(\rho_a/\rho_f)^{0.5}$$

Substituting for Hv from Equation 6 and $(\rho_f)^{-0.5}$ from Equation 4 we have:

$$Wo = K_1(Q_a/Q_f)(\rho_a)^{0.5} Q_f / K(\Delta P)^{0.5} \quad (8)$$

Simplifying Equation 8:

$$Wo = K_1 Q_a (\rho_a)^{0.5} / K(\Delta P)^{0.5} \quad (9)$$

Now, $K_1 Q_a \rho_a$ and K are known. Equation 9 becomes $$Wo = K_3 / (\Delta P)^{0.5} \quad (10)$$

It can readily be seen from the above, that by controlling the sample burner mixture at a substantially stoichiometric air-fuel ratio and monitoring the ΔP of the fuel the Wobbe number can readily be determined providing an instantaneous readout for display, recording or control purposes.

Figure 3:
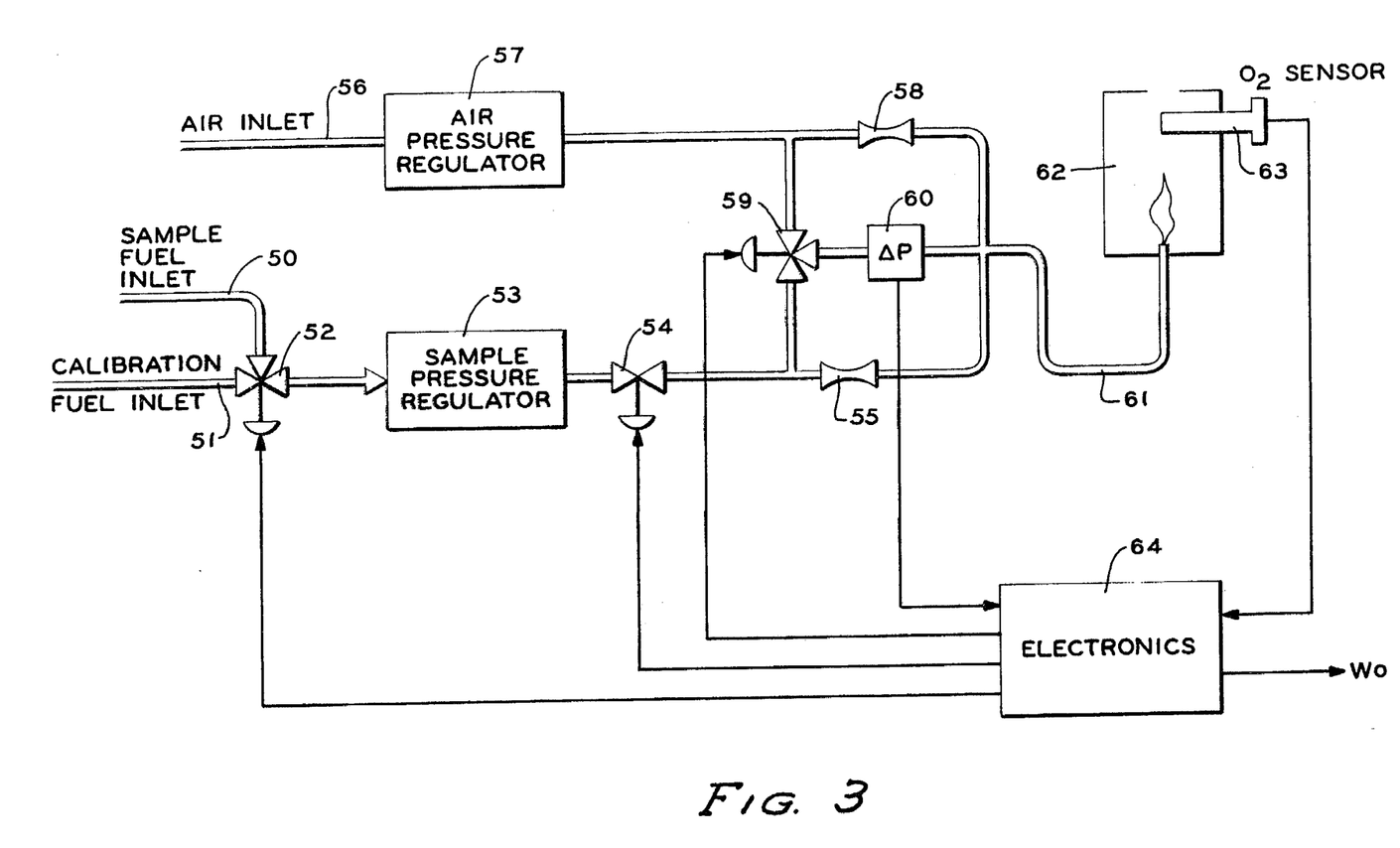
FIG. 3 is a schematic diagram of an alternate embodiment of the invention.
Figure 4:
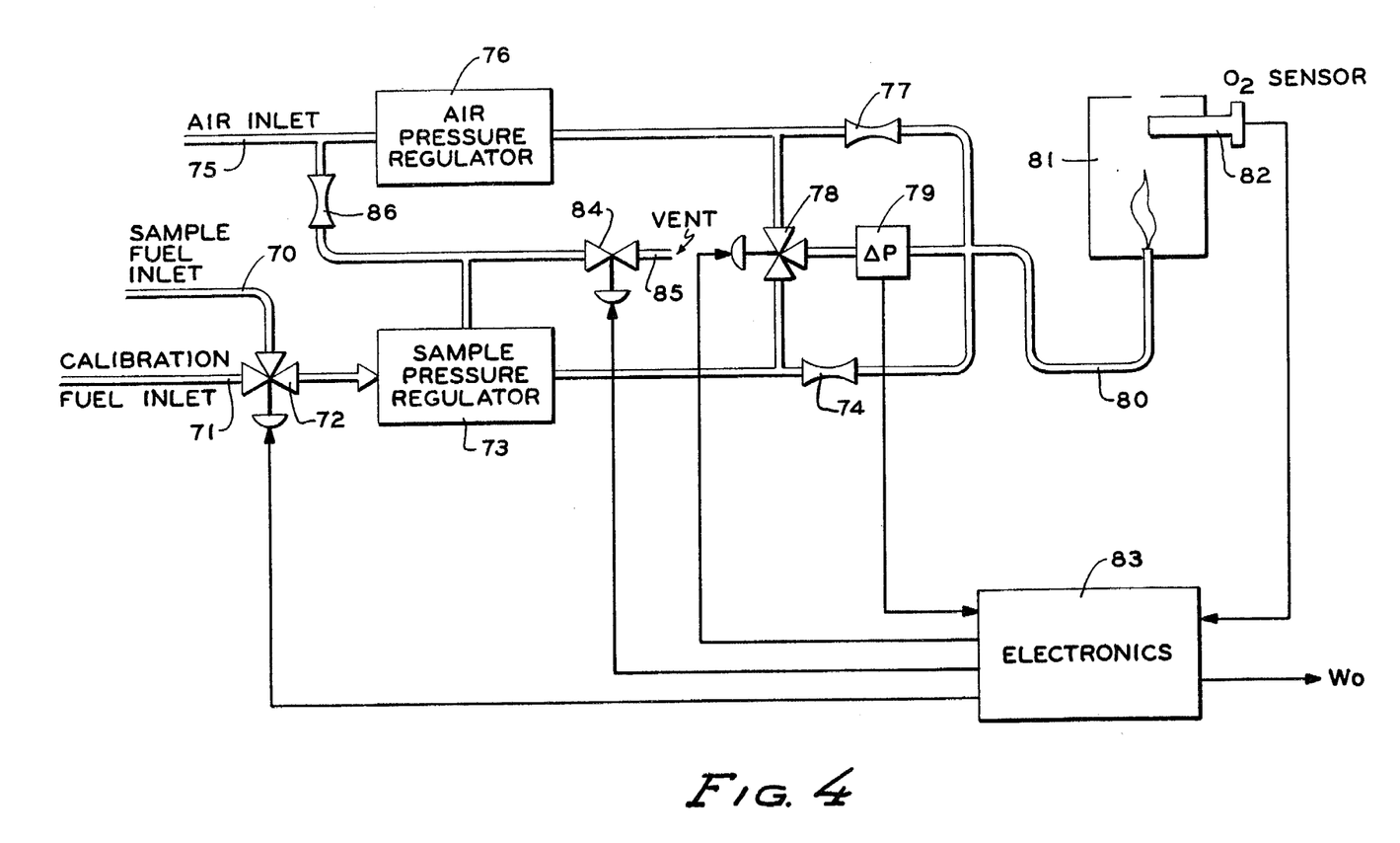
FIG. 4 is a schematic diagram of variation of the embodiment of FIG. 3.
Figure 5:
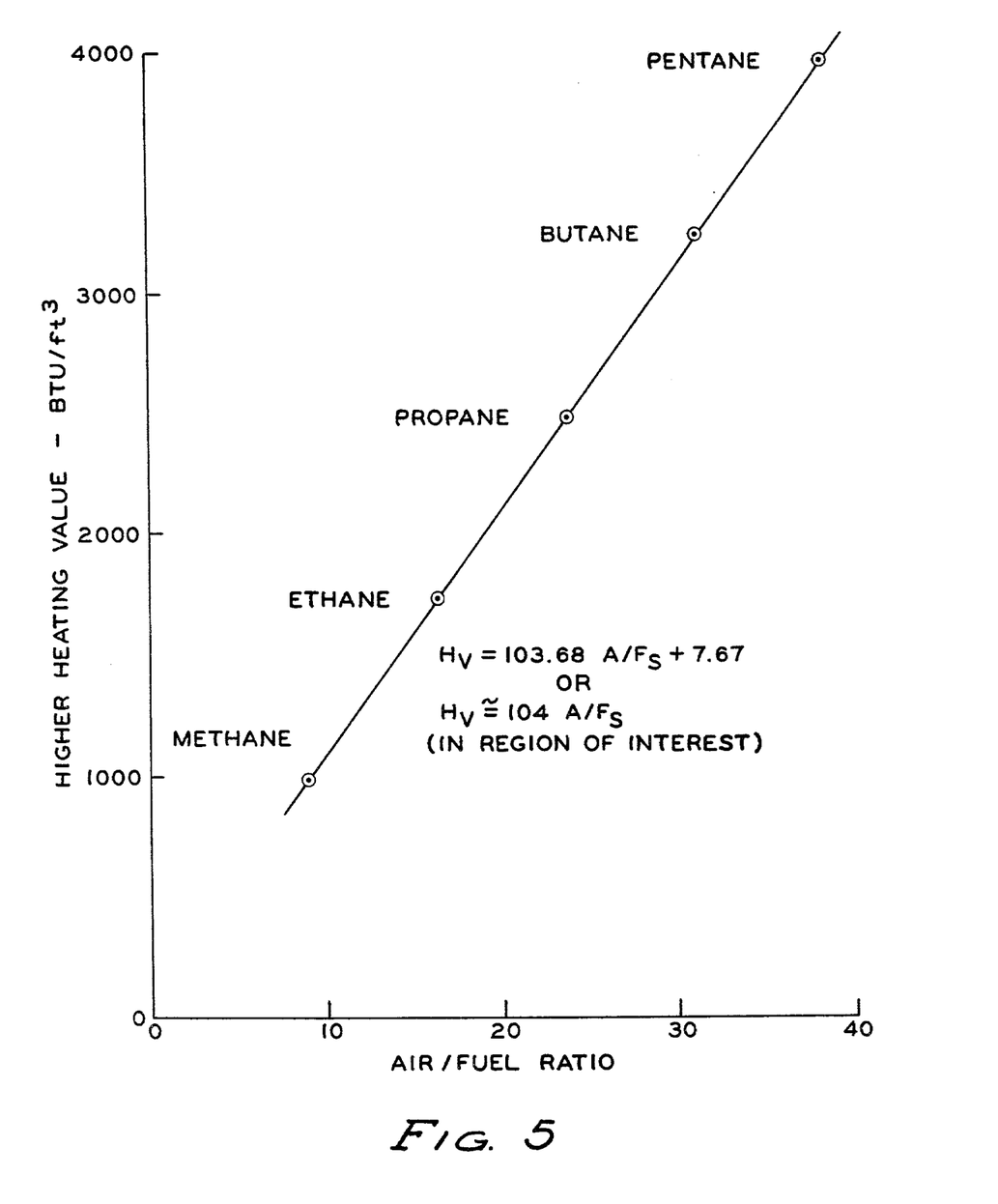
FIG. 5 is a plot showing the heat content of various hydrocarbon fuels.
Figure 6:
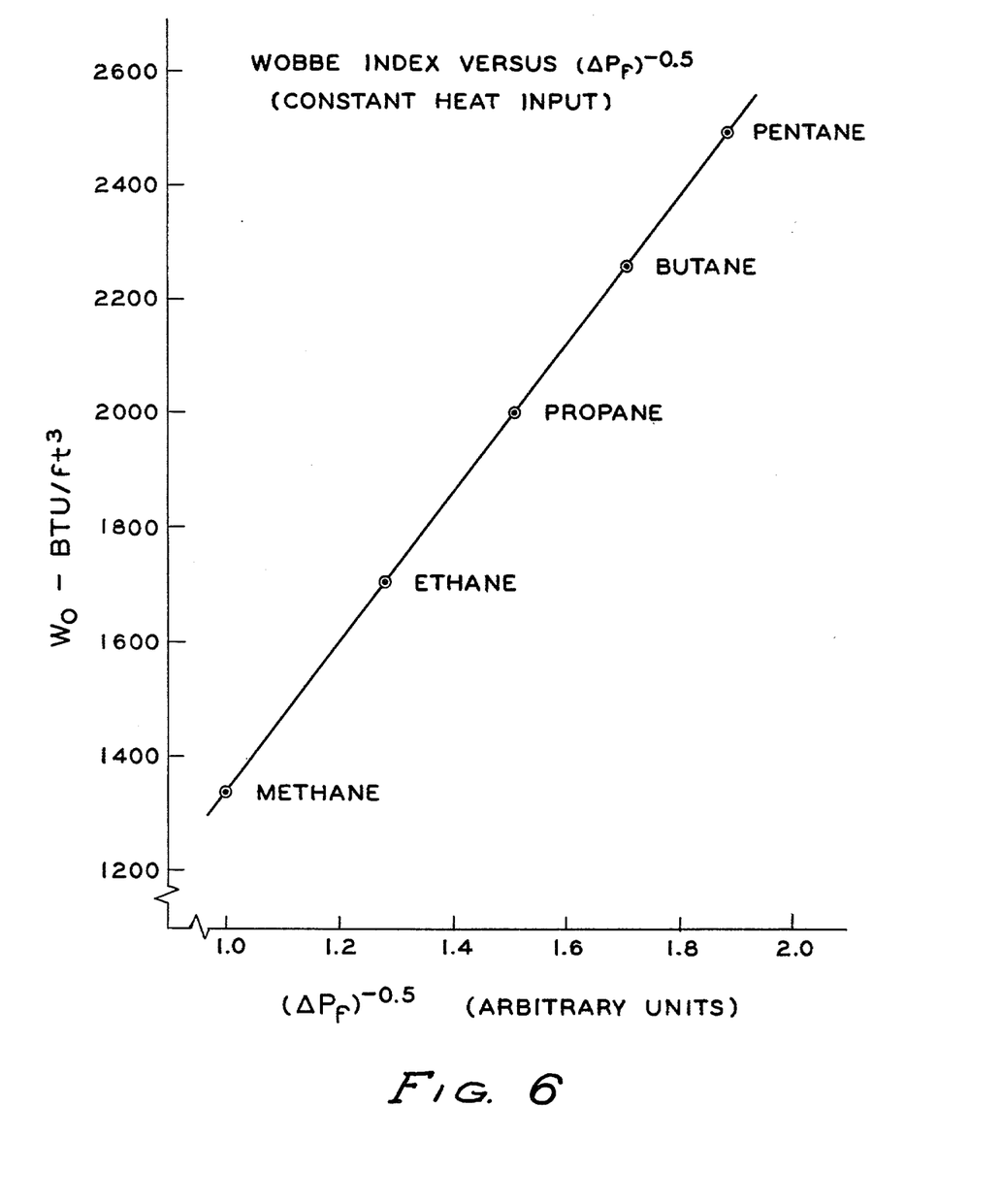
FIG. 6 is a plot of the Wobbe number for constant heat input versus fuel gas flow based on the reciprocal square root of the orifice pressure drop in arbitrary units normalized to methane, and FIG. 7 as a representative curve of the signal response in millivolts versus the air-fuel ratio of a typical $ZrO_2$ sensor used in accordance with the invention.

FIGS. 3 and 4 contain schematic diagram representations of variations of an alternate embodiment of the present invention. The embodiment of FIG. 3 includes a sample fuel inlet 50 which, with calibration gas inlet 51, supplies either sample fuel or calibration gas to the system through a two-position, three-way valve 52 which may be electrically controlled to admit the selected component to the system through pressure regulator 53. A flow control valve 54, which, like that of the embodiment described in conjunction with FIG. 1, may be any suitable type of flow control valve, the flow through which can be accurately modulated electrically, is provided to control the sample flow to the system. In addition, a metering orifice 55 is also provided.

Combustion air is supplied this system through an air inlet 56 in conjunction with an air pressure regulator 57 and metering orifice 58. A second two-position, three-way remotely controlled valve 59 is provided in conjunction with metering orifice pressure transducer 60 to allow accurate pressure differential measurement of the flow through either metering orifice 55 or 58, respectively. The metered air and fuel proceed through and are mixed in conduit 61 which conveys them to combustion chamber 62 containing oxygen sensor 63. An electronics package shown at 64 is also provided. The combustion system oxygen sensing system may be the same as those discussed previously with regard to the first embodiment of the present invention.

A variation of the embodiment of FIG. 3 is illustrated in FIG. 4 which includes sample fuel inlet 70, calibration gas inlet 71, two-position, three-way valve 72, pressure regulator 73 and orifice 74. Similarly, inlet air system includes a source of combustion air 75, air pressure regulator 76 and orifice 77. The system also contains a second two-position three-way valve 78 operated in conjunction with orifice pressure transducer 79, inlet mixing conduit 80, combustion chamber 81 and exhaust gas sensor 82 and electronic package 83.

This alternate embodiment replaces the flow control valve in the sample gas inlet flow control valve 54 of FIG. 3 with flow control valve 84 which also may be any suitable flow control valve, the flow through which can be precisely modulated electrically. That valve is open to a vent as at 85 and controls the flow through the sample pressure regulators 73 via a connection to the air inlet system through an orifice 86 connected both to the vent valve 83 and the sample pressure regulator 73.

In this embodiment of the Wobbe Index of the present invention, the sample flow rate is adjusted by means of control valve connected in such a way that air is bled off at a variable ratio to control the pressure on the top of the fuel regulator thereby controlling the fuel pressure and fuel flow rate. This control scheme like that of FIG. 2 offers the advantage of eliminating the concern of leaking fuel which may take place about the needle valve 54 of the embodiment of FIG. 3 and enables the fuel output pressure of the regulator to be placed across the metering orifice.

The embodiment of FIGS. 3 and 4 operates basically in the same manner as the embodiment of FIGS. 1 and 2, i.e., the sample of fuel and air is burned in the closed combustion chamber and the products of combustion are sensed by the sensor. A conventional electronic controller found in the electronics package, in a conventional manner based on the sensor output continually adjusts the sample fuel valve such that the fuel supplied enables the burner to burn at substantially stoichiometric combustion conditions as determined by the sensor. However, the ability to measure the flow of both the air and the gas in rapid succession via the second two-position, three-way valve in an associated pressure measuring transducer enables the Wobbe Index to be determined using the measured pressure drop across both the fuel flow and air flow orifices as determined by the following expression:

$$W_o = K_4 (\Delta p_a / \Delta p_f)^{0.5} \qquad (11)$$

The constant K may be determined by burning a certified standard gas of known Wobbe Index number and then:

$$K_4 = W_{oStd} (\Delta p_{fStd} / \Delta p_{aStd})^{0.5} \qquad (12)$$

Where $\Delta p_{fStd}$ is the differential pressure of standard gas and $\Delta p_{aStd}$ is the differential pressure of the air when testing the standard gas assuming the fuel temperature and air temperature are the same. Pressure measurements can be made with a pressure transducer, such as a Catalog Number 142PC01D now available from Honeywell Inc. Microswitch Division, Freeport, Ill., that has a repeatable resolution of 1 part in 1000. It should be noted that the pressure transducer does not have to be accurate or calibrated, but is only required to have good repeatability and not drift between calibration and use.

It is readily understood that the foregoing description with regard to the embodiment of the invention assumes that the air or oxidizing gas and the fuel are at the same temperature when passing through the metering devices. This is normally the case as both are exposed to the same ambient conditions. However, if for any reason this is not the case, suitable temperature sensors may be provided and proper temperature compensation made in a well-known manner.

It can readily be seen from the above that either of the embodiments including the alternatives thereof clearly lend themselves to simple, accurate, repeatable systems for determining the Wobbe Index of gaseous hydrocarbon fuels. The output can be utilized in any manner such information is desired by conventional means. The electronics package associated with the various embodiments of the present invention can be either a hardwired system or a conventional microprocessor system programmed to provide the necessary control and readout functions in a well-known manner.

The embodiments of the invention in which an exclusive property or right is claimed are defined as follows:

1. Apparatus for determining the Wobbe Index of gaseous fuels comprising:
   means for supplying a gaseous fuel sample and a substantially constant amount of air to provide a combustible mixture thereof;
   means for determining the pressure differential of a flowmeter through which said fuel constituent of said mixture is caused to flow;
   burner means for the combustion of said mixture;
   means for sensing the presence of combustibles or oxygen in the products of combustion of said mixture, wherein said sensing means is one exhibiting a rapid change in output signal about a particular combustion product composition wherein said output is quantitatively indicative of a certain relative amount of said combustibles or oxygen in said products of combustion;

means for adjusting the relative amount of fuel in said mixture in response to the output of said sensing means until said sensing means indicates that said products of combustion contain said certain relative amount of said combustibles or oxygen;

means for determining the Wobbe Index of said fuel from a known relationship between the heating value of the fuel constituents and the amount of oxygen required for the combustion thereof at said particular combustion product composition and the pressure differential across said fuel flowmeter means.

2. The apparatus of claim 1 wherein said pressure differential flowmeter means is an orifice meter.

3. The apparatus of either of claims 1 or 2 wherein said rapid change in sensor signal output occurs substantially at the point of stoichiometry with respect to the sample mixture.

4. The apparatus of claim 3 wherein said sensor is made substantially of $ZrO_2$ stabilized by a compound substantially consisting of one or more of the following: CaO, MgO and $Y_2O_3$.

5. The apparatus of claim 4 wherein said stabilizing compound consists substantially of CaO.

6. The apparatus of claim 1 wherein said means for adjusting said relative amount of fuel in said mixture is an electrically modulated flow control valve in the fuel input line.

7. Apparatus for determining the Wobbe Index of gaseous fuels comprising:
means for establishing a mixture of gaseous fuel sample with air further comprising,
a source of air at regulated pressure;
a source of sample fuel at regulated pressure;
a source of calibration fuel of known Wobbe Index at regulated pressure;
means for determining the pressure differential of a flowmeter through which said air constituent of said mixture is caused to flow;
means for determining the pressure differential of a flowmeter through which said fuel constituent of said mixture is caused to flow;
burner means for the combustion of said mixture;
sensing means for sensing the presence of combustibles or oxygen in the products of combustion of said mixture, wherein said sensing means is one exhibiting a rapid change in output signal about a particular combustion product composition wherein said output quantitatively indicative of a certain relative amount of said combustibles or oxygen in said products of combustion;
means for adjusting the relative amount of fuel in said mixture in response to the output of said sensing means until said sensing means indicates that said products of combustion contain said certain relative amount of said combustibles or oxygen;
means for determining the Wobbe Index of said fuel from a known relationship between the pressure differential across said fuel and said air flowmeter means and the Wobbe Index of said calibration fuel.

8. The apparatus of claim 8 wherein said pressure differential flowmeter means is an orifice meter.

9. The apparatus of either of claims 8 or 9 wherein said rapid change in sensor signal output occurs substantially at the point of stoichiometry with respect to the sample mixture.

10. The apparatus of claim 10 wherein said sensor is made substantially of $ZrO_2$ stabilized by a compound substantially consisting of one or more of the following: CaO, MgO and $Y_2O_3$.

11. The apparatus of claim 11 wherein said stabilizing compound consists substantially of CaO.

12. The apparatus of claim 8 wherein said means for adjusting said relative amount of fuel in said mixture is an electrically modulated flow control valve in the fuel input line.

13. The apparatus of either of claims 1 or 7 wherein said means for adjusting said relative amount of fuel in said mixture comprises
a pressure regulator in the fuel input line, said regulator being backloaded from the air supply line supplying air to said mixture upstream of any regulator therein; and
an electrically modulated flow control valve having an inlet port in common with the backloading line and an output port connected to a vent means such that the back pressure on said regulator may be accurately controlled.

14. A method for determining the Wobbe Index of gaseous fuels comprising steps of:
supplying a gaseous fuel sample and air to provide a combustible mixture thereof, said air being of substantially constant amount;
monitoring the pressure differential of the flow of said gaseous fuel sample through a flowmeter;
burning said sample in the presence of a means for sensing the presence of combustibles or oxygen in the products of combustion of said mixture, using a sensing means exhibiting a rapid change in output signal about a particular combustion product composition wherein said output is quantitatively indicative of a certain relative amount of combustibles or oxygen in the products of combustion;
adjusting the relative amount of fuel in said mixture in response to the output of said sensing means until said sensing means indicates that said products of combustion contain said certain relative amount of said combustibles or oxygen;
determining the Wobbe Index of said fuel from a known relationship between the heating value of the fuel constituents and the amount of oxygen required for the combustion thereof at said particular combustion product composition and the pressure differential across said fuel flowmeter means.

* * * * *

UNITED STATES PATENT OFFICE
CERTIFICATE OF CORRECTION

PATENT NO. : 4,359,284
DATED : November 16, 1982
INVENTOR(S) : William B. Kude and A. Noel J. Pearman It is certified that error appears in the above-identified patent and that said Letters Patent are hereby corrected as shown below:

Column 12, line 8, "8" (second occurrence) should read --7--.

Column 12, line 10, "8 or 9" should read --7 or 8--.

Column 12, line 14, "10" (second occurrence) should read --7--.

Column 12, line 18, "11" (second occurrence) should read --10--.

Signed and Sealed this

Seventeenth Day of May 1983

[SEAL]

Attest:

DONALD J. QUIGG

Attesting Officer    Acting Commissioner of Patents and Trademarks